United States Patent [19]
Evetts et al.

[11] Patent Number: 6,019,994
[45] Date of Patent: Feb. 1, 2000

[54] USE OF LEVOBUPIVACAINE IN TREATING MIGRAINE

[75] Inventors: Ian Ashley Evetts; Simon John Gunning, both of Cambridge, United Kingdom

[73] Assignee: Chirotech Technology, Ltd., United Kingdom

[21] Appl. No.: 09/034,081

[22] Filed: Mar. 3, 1998

[30] Foreign Application Priority Data

Mar. 3, 1997 [GB] United Kingdom ............... 9704349

[51] Int. Cl.$^7$ ............................. A61F 13/00; A61F 9/02
[52] U.S. Cl. ......................... 424/434; 424/435; 424/436
[58] Field of Search ............................................ 424/431

[56] References Cited

U.S. PATENT DOCUMENTS 4,695,576   9/1987   af Ekenstam et al. .

FOREIGN PATENT DOCUMENTS

| 2135673 | 2/1998 | United Kingdom . |
| 9510276 | 4/1995 | WIPO ..................................... 31/445 |
| 9632109 | 10/1996 | WIPO . |
| 9903473 | 1/1999 | WIPO . |

OTHER PUBLICATIONS

Maizels, M et al. "Intranasal lidocaine for treatment of migraine" JAMA 319–321, Jul. 24, 1996.
Butterworth, J. F. et al. (1993) "Bupivacaine Inhibits Cyclic–3', 5' Adenosine Monophosphate Production" Anesthesiology 79:88–95.
Mazoit, J. X. et al. (1993) "Myocardial Uptake of Bupivacaine: II Pharmacokinetics and Pharmacodynamics of Bupivacaine Enantiomers in the Isolated Perfused Rabbit Heart" Anesth. Analg. 77(3):477–482.
Clarkson, C. W. et al. (1985) "Mechanism for Bupivacaine Depression of Cardiac Conduction: Fast Block of Sodium Channels during Action Potential with Slow Recovery from Block during Diastole" Anesthesiology 62:396–405.
Courtney, K.R. et al. (1988) "Bupivacaine is an effective potassium channel blocker in heart" Biochimica et Biophyscia Acta 939:163–166.
Denson, D. D. et al. (1992) "Enantiomer–Specific Effects on an Intravenously Administered Arrhythmogenic Dose of Bupivacaine on Neurons of the Nuleus Tractus Soluatroius and the Cardiovascular System in the Anesthetized Rat" Regional Anesthesia 17:311–316.
Vanhoutte, F. et al. (1991) "Stereoselective effects of the enantiomers of bupivacaine on the electrophysiological properties of the guinea–pig papillary muscle" Br. J. Pharcacol. 103:1275–1281.
Valenzuela, C. et al. (1994) "Stereoselective Bupivacaine Block of the Human Cardiac Delayed Rectifier Kv1.5 Channel" Biophys. J. 66:A205, abstract No. Tu–Pos383.
Aps, C. et al. (1978) "An Intradermal Study of the Local Anaesthetic and Vascular Effects of the Isomers of Bupivacaine" Br. J. clin. Pharmac. 6:63–68.

Burm, A.G.L. et al.(1994) "Pharmacokinetics of the enantiomers of bupivacaine following intravenous administration of the racemate" Br. J. Clin. Pharmac. 38:125–129.
Reynolds, F. (1995) "In defence of bupivacaine" International Journal of Obstetric Anesthesia 4:93–108.
Kuhnert, B.R. et al. (1981) "Bupivacaine disposition in mother, fetus, and neonate" Federation Proceedings, vol. 40, No. 31, p. 684.
Ariens, E. J. (1991) "Racemic therapeutics–ethical and regulatory aspects" Eur. J. Clin. Pharmacol., vol. 41, No. 2, pp. 89–93.
Rutten, A. J. et al. (1991) "Cardiovascular Effects and Regional Clearances of I.V. Bupivacaine in Sheep: Enantiomeric Ananlysis" Br. J. Anasth., vol. 67(3):247–256.
Luduena, A. J. et al. (1972) "Optical Isomers of Mepivacaine and Bupivacaine" Arch. Int. Pharmacodyn. Ther., 200(2):359–369.
Rutten, A. J. et al. (1992) "Postoperative course of plasma protein binding of lignocaine, ropivacaine and bupivacaine in sheep" J. Pharm. Pharmacol., 44(4):355–358.
Lee–Son, S. et al. (1992) "Stereoselective Inhibition of Neuronal Sodium Channels by local Anaesthetics" Anesthesiology, 77(2):324–335.
Wang, G. K. et al. (1992) "Altered Stereoselectivity of Cocaine and bupivacaine Isomers in Normal and Barachotoxin–modified Na+ Channels" J. Gen. Phsysiol., 100(6):1003–1020.
Chemical Abstracts, 73(5), Aug. 3, 1970, Columbus, Ohio, U.S.; abstract No. 25314a.
Clark, B. J. et al. (1991) "Reversed–phase and chiral high–performance liquid chromatographic assay of bupivacaine and its enantiomers in clinical samples after continuous extrapleural infusion" J. Chromatog., 553:383–390.
Ariens, E. J. (1990) "Racemische therapeutica probleemmiddelen" Pharmaceutisch Weekblad, 125(2):552–554.
Areiens, E. J. (1990) "Stereoselectivity in pharmacodynamics and pharmacokinetics" Schweiz. med. Wochenschr., 120(5):131–134.
Rowland, M. et al.(eds.) In: Clinical Pharmacokinetics Concepts and Applications, Chapter 7, pp. 83–88, (1995) Williams & Wilkins publishers.
Mather, L. E. (1991) "Disposition of Mepivacaine and Bupivacaine Enantiomers In Sheep" British Journal of Anaesthesia 67:239–246.
Du Pen, S. L. et al. (1992) "Chronic epidural bupivacaine–opioid infusion in intractable cancer pain" Pain 49:293–300.
Honerjäger, P. (1986) "The contribution of Na channel block to the negative inotropic effect of antiarrhythmic drugs" Basic Res. Cardiol. 81 (Suppl 1):33–37.
Fozzard, H.A. et al. (1985) "Voltage Dependence of Intracellular Sodium and Control of Contraction" In Zipes DP, Jalife E (eds) Grune & Stratton, Orlando, pp. 51–57.

(List continued on next page.)

Primary Examiner—Thurman K. Page
Assistant Examiner—Todd D Ware
Attorney, Agent, or Firm—Saliwanchik, Lloyd & Saliwanchik

[57] ABSTRACT

Levobupivacaine or ropavicaine is used to treat migraine.

2 Claims, No Drawings

OTHER PUBLICATIONS

Schlepper, M. (1989) "Cardiodepressive effects of antiarrhythmic drugs" European Heart Journal 10(Suppl. E.):73–80.

Reiz, S. et al. (1986) "Cardiotoxicity Of Local Anaesthetic Agents" Er. J. Anaesth. 58:736–746.

De Jong, R. H. et al. (1981) "Treating Bupivacaine Arrhythmias: Preliminary Report" Reg Anesth 6:99–103.

Strichartz, G. R. (1988) :Neural physiology and local anesthetic action In: Neural Blockade In Clinical Anesthesia And Management Of Pain, Cousins MJ, Bridenbaugh PO (eds), J B Lippincott Company, Philadelphia, pp. 25–45.

Testa, B. et al. (1990) "Racemates Versus Enantiomers in Drug Development: Dogmatism or Pragmatism?" Chirality 2:129–133.

Rutten, A. J. et al. (1993) "Tissue distribution of bupivacaine enantiomers in sheep" Chirality 5(7):485–491.

Aberg, G. (1972) "Toxicological and local anaesthetic effects of optically active isomers of two anaestheitic compounds" Acta Pharmacologica Et Toxicologica 31:273–286.

Gristwood, R. et al. (1994) "Reduced cardiotoxicity of levobupivacaine compared with racemic bupivacaine (Marcaine): new clinical evidence" Exp. Opin. Invest. Drugs 3(11):1209–1212.

Barth, M. et al. (1984) "Effects of Application of I.V. with Local Anaesthesia on Chronic Pain Syndromes, Especially Headache and Migraine" Pain p. S269 Abstract.

USE OF LEVOBUPIVACAINE IN TREATING MIGRAINE

FIELD OF THE INVENTION

This invention relates to a new therapeutic use for ropivacaine and levobupivacaine.

BACKGROUND OF THE INVENTION

Racemic bupivacaine is an effertive long-acting local anaesthetic, and may be given as an epidural. However, racernic bupivacaine is cardiotoxic, having depresant electrophysiological and mechanical effects on the heart. It should therefore be used with caution in cardiac-compromised patients, and the use of high doses and high concentrations is contraindicated.

In particular, bupivacaine has produced death in a number of patients, including women in childbirth and when used in the Bier's block technique. Although the incidence of death has been relatively small, the concern has been sufficient, to stop the use of 0.75% bupivacaine for obstetrics and the proscribing of bupivacaine for use in Bier's blocks.

In addition, due to its mode of action, directly on the nervous system at higher doses, bupivacaine is known to have undesirable central nervous system (CNS) side-effects which, prima facie, are connected to its anaesthetic activity. Indeed, the occurrence of CNS side-effects is one of the major factors limiting the use of this drug in normal clinical practice employing techniques such as local infiltration, nerve block, field block, epidural and spinal blocks.

It has been suggested that levobupivacaine is less cardiotoxic than dextrobupivacaine and racemic bupivacaine. See, for example, Vanhoutte et al, Br. J. Pharmacol. 103:1275–1281 (1991), and Denson etal, Regional Anaesthesia, 17:311–316 (1992). However, these reports are based on work in vitro, and cannot necessarily be extrapoled to any mammals, and certainly not to humans.

The surprising and effective utility of levobupivacaine in man, in vivo, is evidenced for the firs, time in WO-A-95 10276, WO-A-9510277 and Gristwood et al, Exp. Opin. Invest. Drugs 3(11):1209–12 (1994).

Bupivacaine has been tested, for the treatment of migraine, by infusion of 0.2 mg/kg. Some reliefwas reported. See Pain (1984), Suppl. 2S269. This possibility has not been developed.

SUMMARY OF THE INVENTION

While it has previously been shown that the use of levobupivacaine may have advantages over bupivacaine in certain areas, there has been no evidence to suggest that it would be of value, in migraine. This invention is based on the surprising discovery that levobupivacaine and ropivacaine may be effective drugs, for this purpose.

DESCRIPTION OF THE INVENTION

For the purposes of this specification, migraine may be defined as in Dorland's Illustrated Medical Dictionary, 27th Edition, i.e. an often familial symptom complex of periodic attacks of vascular headache, usually temporal and unilateral in onset, commonly associated with irritability, nausea, vomiting, constipation or diarrhoea, and often with photophobia; attacks are preceded by constriction of the cranial arteries, usually with resultant prodromal sensory (especially ocular) symptoms, and commence with the vasodilation that follows. Migraine can be broken down into various specific types including: abdominal, acephalic, acute confusional, basilar, classic, common, complicated, fulgurating, Harris', hemiplegic, ocular, ophthalmic and ophthalmoplegic.

Activity in migraine can be demonstrated by showing that either or both drugs (which are, chemically, homologues) have potency as agonists at $5HT_1$ receptors in vitro, or show potency in any other in vitro test for migraine or potency in animal models of migraine. A suitable model is used in the study that is reported below.

In the method of the present invention, levobupivacaine or ropivacaine may be provided in solution, for infusion, e.g. intravenously, or installation, as eye drops, nasal drops/spray, in an intradermal patch, injection, or as any preparation for infiltration, peripheral or central administration, e.g. topical, subcutaneous or epidural administratior Oral or rectal administration may also be used.

Administration of levobupivacaine or ropivacaine may be continuous or bolus administration. This may be done using conventional apparatus, e.g. including means for the patient to induce infusion as desired. The daily dose administered to the patient may be in the relatively low range known for the administration of racemic bupivacaine, but, because of the decreased CNS side-effects of Levobupivacaine, may be higher than the conventional dose for the racemic drug. The total dose of levobupivacaine may be around, or in excess of 2 mg per kg of patient body weight.

The concentration of levobupivacaine to be given can be that conventionally used for the racemic drug. However, the concentration is typically higher than this, for instance, at least 0.75% w/v, and can be up to 2% w/v. Preferably, however, the concentration of levobupivacaine is in the range 0.8% to 1.5% w/v, and more preferably a concentration of 1%, 1.25% or 1.5% w/v is used. The solution is preferably aqueous.

The solution may typically be put up in unit doses of from 1 to 15 ml, and preferably of around 10 ml. However, the unit doses may be higher, for instance up to 40 ml or higher. The unit doses may be in the form of ampoules, which may be made of any suitable material, e.g. glass or an appropriately impervious plastics material. Unit dosages comprising, at least 75 mg, but preferably less than 200 mg, of levobupivacaine can be administered, and more preferably the unit dosage is in the range 80 to 150 mg.

The administration of levobupivacaine over a range of concentrations, including those currently used for the racemic drug and the higher concentrations described above, can be carried out for significantly longer periods than at present, again as a result of the reduced CNS side-effects experienced with levobupivacaine. For instance, levobupivacaine can be administered to a patient safely for at least 24 hours, often up to 72 hours, and even for periods of up to a week or a fortnight, or longer. It can, of course, be administered for similar periods already used for the racemic drug, e.g. between 0.5 and 6 hours.

For the purposes of the present specification, the levobupivacaine is substantially free of dextrobupivacaine, i.e. in at least 90%, and most preferably at least 99%, enantiomeric excess. Throughout this specification, reference to bupivacaine and its enantiomers includes pharmaceutically-acceptable salts thereof Ropivacaine may be substituted for levobupivacaine, where the latter only has been discussed above.

A study has been conducted, in order to compare the abilities of levobupivacaine, bupivacaine and dextrobupivacaine to contract human isolated cerebral vascular smooth muscle. More specifically, this study investigates the effect of levobupivacaine, bupivacaine and dextrobupivacaine on basal tone of isolated rings of human cerebral artery, with each compound being tested in duplicate in tissues from three separate donors.

Eight preparations from each donor were dosed in a cumulative manner with a thromboxane $A_2$ mimetic (1 nM–1 $\mu$M). All preparations responded by contracting in a concentration-dependent manner.

In two separate preparations from each donor, a cumulative concentration-effect curve was obtained, at a concentration of 1 nM–10 $\mu$M. Following the maximum dose of the test compounds, a further concentration-effect curve was obtained in all preparations. In the two remaining preparations from each donor, the second concentration-effect curve was obtained in the absence of test compounds.

In six preparations from the three donors, application of bupivacaine or dextrobupivacaine had no significant effect on basal tone, even at a concentration of 10 $\mu$M. However, for levobupivacaine, there was an apparent small contraction at a concentration of 10 $\mu$M.

In the presence of bupivacaine or dextrobupivacaine, and on preparations untreated with the test compounds, a second concentration-effect curve to the $TXA_2$ mimetic was not significantly different from the first curve. In tissues treated with levobupivacaine, however, there was a modest increase in the maximum response to the mimetic.

These results demonstrate that whereas bupivacaine and dextrobupivacaine have no effect on basal tone of human isolated cerebral vascular smooth muscle, or on the response to a $TXA_2$ mimetic, levobupivacaine does show a tendency to increase both basal tone and responses to subsequently applied mimetic. On the basis of this model, levobupivacaine has surprising properties that are likely to he of benefit, in the treatment of migraine. These properties may be expected for ropivacaine, by comparison with that compound mixed with its opposite enantiomer, i.e. its racemic form.

We claim:

1. A method for treating migraine in a patient, said method comprising administering an effective amount of levobupivacaine or ropivacaine to said patient, wherein said levobupivacaine or ropivacaine is administered intranasally, and wherein said levobupivacaine or said ropivacaine is present in an enantiomeric excess of at least about 90%.

2. The method, according to claim 1, wherein said solution of levobupivacaine or ropivacaine is administered as drops or a spray.

* * * * *